US008969562B2

(12) United States Patent
Kruger et al.

(10) Patent No.: US 8,969,562 B2
(45) Date of Patent: Mar. 3, 2015

(54) AZAADAMANTANE FORMATE ESTER AND PROCESS FOR PREPARING AZAADAMANTANE DERIVATIVES

(71) Applicant: AbbVie Inc., North Chicago, IL (US)

(72) Inventors: Albert Wayne Kruger, Pleasant Prairie, WI (US); Shuang Chen, Gurnee, IL (US); Steven Cramer Cullen, Lake Villa, IL (US); James Joseph Napier, Antioch, IL (US)

(73) Assignee: AbbVie, Inc., North Chicago, IL (US)

( * ) Notice: Subject to any disclaimer, the term of this patent is extended or adjusted under 35 U.S.C. 154(b) by 0 days.

(21) Appl. No.: 14/204,356

(22) Filed: Mar. 11, 2014

(65) Prior Publication Data

US 2014/0275546 A1 Sep. 18, 2014

Related U.S. Application Data

(60) Provisional application No. 61/777,785, filed on Mar. 12, 2013.

(51) Int. Cl.
| | | |
|---|---|---|
| *C07D 285/135* | (2006.01) | |
| *C07D 285/12* | (2006.01) | |
| *C07D 471/18* | (2006.01) | |
| *C07C 249/02* | (2006.01) | |

(52) U.S. Cl.
CPC ............ *C07D 471/18* (2013.01); *C07C 249/02* (2013.01); *C07D 285/12* (2013.01); *C07D 285/135* (2013.01)
USPC ......................................................... 546/74

(58) Field of Classification Search
USPC .......................................................... 546/74
See application file for complete search history.

(56) References Cited

U.S. PATENT DOCUMENTS

| | | | | |
|---|---|---|---|---|
| 4,251,664 | A | 2/1981 | Spitzner | 548/138 |
| 5,086,503 | A | 2/1992 | Chung et al. | 395/700 |
| 7,902,222 | B2 | 3/2011 | Ji et al. | 514/304 |
| 8,163,916 | B2 | 4/2012 | Schrimpf et al. | 546/97 |
| 8,314,119 | B2 * | 11/2012 | Schrimpf et al. | 514/294 |
| 2012/0245195 | A1 | 9/2012 | Chen et al. | 514/294 |

OTHER PUBLICATIONS

Greene et al., (1999), "Protective groups in organic synthesis", Third Edition, Wiley and Sons, ISBNs: 0-471-16019-9 (Hardback); 0-471-22057-4 (Electronic).

Hoggarth, (1949), "Compounds related to thiosemicarbazide. Part II 1-Benzoylthiosemicarbazides", *J. Chem. Soc.*, pp. 1163-1167.

Kimpe et al., (1997), "Synthesis of 3-alkenylamines, 4-alkenylamines and 3-allenylamines via a transamination procedure", *Tetrahedron*, vol. 53, 31, pp. 10803-10816.

Levin, E., (2002), "Nicotinic receptor subtypes and cognitive function Developmental Neurobiology", *J. Neurobiol.* 53:633-640.

Paterson et al., (2000), "Neuronal nicotinic receptors in the human brain", *Progress in Neurobiology*. 61:75-111.

Renshaw, S. (2007), Chapter 4 "Immunochemical staining techniques, Immunohistochemistry", *Scion Publishing Ltd*, Bloxham, UK, 1:48-50.

Udding et al., (1994), Copper-Catalysed N-Acyliminium Ion Cyclisation to 3-Azabicyclo[3.3.1]nonanes; Synthesis of 2,4-Distributed 1-Aza-adamantanes, *Tetrahedron*, vol. 50, 29: pp. 8853-8862.

* cited by examiner

*Primary Examiner* — Niloofar Rahmani

(74) *Attorney, Agent, or Firm* — Harness, Dickey & Pierce, P.L.C.

(57) ABSTRACT

A compound, (4s)-1-azaadamantane-4yl formate ester, is described. In addition, a process is described for preparing (4s)-1-azaadamantane-4yl formate ester, aminothiadiazole-phenyl phosphate salt, bromothiadizole-phenyl or (4s)-4-(5-phenyl-1,3,4-thiadiazol-2-yloxy)-1-azatricyclo[$3.3.1.1^{3,7}$]-decane dihydrogen citrate. Furthermore, a process is described, comprising step of hydrolyzing (4s)-1-azaadamantane-4yl formate ester to form (4s)-1-azaadamantan-4-ol HBr salt.

5 Claims, No Drawings

AZAADAMANTANE FORMATE ESTER AND PROCESS FOR PREPARING AZAADAMANTANE DERIVATIVES

FIELD

Azaadamantane derivatives and a process for preparing azaadamantane derivatives are described. More particularly, azaadamantane formate ester intermediate is described. Additionally, processes for preparing the azaadamantane formate ester intermediate and azaadamantanol are described. Furthermore, a process is described for preparing a thiadiazole phosphate salt and a bromo-thiadiazole as intermediates for preparation of phenyl-thiadiazole-azatricyclo-decane compounds.

BACKGROUND

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to, acetylcholine, norepinephrine, dopamine, serotonin, and GABA. Consequently, nicotinic receptors mediate a very wide range of physiological effects, and have been targeted for therapeutic treatment of disorders relating to cognitive function, learning and memory, neurodegeneration, pain, inflammation, psychosis, sensory gating, mood, and emotion, among other conditions.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is comprised of homomeric $(\alpha 7)_5$ (the $\alpha 7$ subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha 7$ and $\alpha 4\beta 2$ nAChRs have been shown to play a significant role in enhancing cognitive function, including aspects of learning, memory and attention (Levin, E. D., J. Neurobiol. 53: 633-640, 2002). For example, $\alpha 7$ nAChRs have been linked to conditions and disorders related to attention deficit disorder, attention deficit hyperactivity disorder (ADHD), schizophrenia, Alzheimer's disease (AD), mild cognitive impairment, senile dementia, dementia associated with Lewy bodies, dementia associated with Down's syndrome, AIDS dementia, and Pick's disease, as well as inflammations. The $\alpha 4\beta 2$ receptor subtype is implicated in attention, cognition, epilepsy, and pain control (Paterson and Norberg, Progress in Neurobiology 61 75-111, 2000), as well as smoking cessation or nicotine withdrawal syndrome.

The activity at both $\alpha 7$ and $\alpha 4\beta 2$ nAChRs can be modified or regulated by the administration of subtype selective nAChR ligands. The ligands can exhibit antagonist, agonist, or partial agonist properties. Compounds that function as allosteric modulators are also known.

Although compounds that nonselectively demonstrate activity at a range of nicotinic receptor subtypes including the $\alpha 4\beta 2$ and $\alpha 7$ nAChRs are known, it would be beneficial to provide compounds that interact selectively with $\alpha 7$-containing neuronal nAChRs, $\alpha 4\beta 2$ nAChRs, or both $\alpha 7$ and $\alpha 4\beta 2$ nAChRs compared to other subtypes.

Recently, azaadamantane derivatives have been investigated for their use as compounds that interact selectively with $\alpha 7$-containing neuronal nAChRs, $\alpha 4\beta 2$ nAChRs, or both $\alpha 7$ and $\alpha 4\beta 2$ nAChRs. Examples of the azaadamantane derivatives include azaadamantane substituted with heteroaryl through an ester or ether linkage. Current synthetic routes to ester- or ether-linked azaadamantane derivatives couple an azaadamantanol intermediate, the synthesis of which is laborious and inefficient, with a halo-containing heteroaryl intermediate.

Hoggarth, J. Chem. Soc., 1163-1167 (1949) shows preparation of 2-amino-5-phenyl-1,3,4-thiadiozole from benzoylthiosemicarbazide and phosphoric acid.

U.S. Pat. No. 4,251,664, filed 24 May 1978, shows preparation of 2-Amino-5-phenyl-1,3,4-thiadiazole from benzoic acid and thiosemicarbazide using concentrated sulfuric acid. Resulting compound is useful for extracting metal from aqueous solution.

U.S. Pat. No. 5,086,503, filed 16 Aug. 1989, describes preparation of amino thiadiazoles of formula

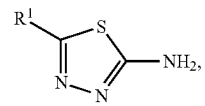

consisting in converting the acid $R^1COOH$ or the acid chloride $R^1COCl$ into the corresponding thiosemicarbazide and in conversion thereof to cyclic form, using a dehydrating agent. The dehydrating agent can be polyphosphoric acid or methane sulfonic acid or sulfuric acid when $R^1$ represents a phenyl group. 2-amino-5-phenyl-1,3,4-thiadiozole is an intermediate to compounds useful for treating senile dementia.

Speckamp et al., Tetrahedron, Vol. 50, No. 29, pg. 8853-8862 (1994), shows synthesis of (4s)-azaadamantanol (an intermediate for synthesis of compounds useful as pharmacologically active agents) from a bicyclic amine 3-azabicyclo [3.3.1]non-6-ene, using paraformaldehyde and formic acid.

Kimpe et al., Tetrahedron, Vol. 53, No. 31, pg. 10803-10816 (1997) shows synthesis of (E)-N-benzylidene-1-(cyclohex-3-en-1-yl)methanamine by condensing cyclohex-3-enecarbaldehyde with benzylamine to give (E)-N-(cyclohex-3-en-1-ylmethylene)-1-phenylmethanamine, followed by an isomerization reaction using potassium tert-butoxide in THF. Resulting isomerized imine is useful as an intermediate for synthesis of agriculture compounds.

U.S. Pat. No. 8,314,119, issued 20 Nov. 2012, shows synthesis of (4s)-1-azaadamantan-4-ol HCl salt from a 7-step process of: (1) Reducing 1,4-dioxaspiro[4.5]decan-8-one with TOSMIC to form 1,4-dioxaspiro[4.5]decane-8-carbonitrile; (2) Reducing resulting product with LAH to form 1,4-dioxaspiro[4.5]decan-8-ylmethanamine; (3) Cyclizing resulting product with a double-Mannich type condensation using paraformaldehyde and sulfuric acid to form azaadamantan-4-one; (4) Reducing the ketone group of azaadamantan-4-one to an alcohol using NaBH₄ in presence of borane-THF complex to form a diastereomer mixture of 1-azaadamantan-4-ol N-borane complex; (5) Coupling resulting product with 4-chlorobenzoic acid; (6) Separating (4s) isomer by column chromatography (silica gel, using 3:1 hexanes-EtOAc), followed by removing 4-chlorobenzoic acid moiety with NaOH; and (7) Removing BH₃ group with HCl giving (4s)-1-azaadamantan-4-ol HCl salt. Alternatively, the (4s)-isomer from Step (6) can be coupled with 2-chloro-5-phenyl-1,3,4-thiadiazole, giving (4s)-4-(5-Phenyl-1,3,4-thiadiazol-2-yloxy)-1-azatricyclo[3.3.1.1$^{3,7}$]-decane N-borane complex. Removal of borane group affords the free base, which was crystallized as a dihydrogen citrate salt. Resulting ether-linked azaadamantane derivative is useful for treating diminished CNS function associated with traumatic brain injury or treating conditions such as arthritis or osteoarthritic pain.

U.S. Pat. No. 8,163,916, issued 24 Apr. 2012, shows synthesis of (4s)-1-azaadamantan-4-ol HBr salt, from a multi-step process of: (1) Reducing a ketone group of azaadamantan-4-one to an alcohol using NaBH₄ in presence of borane-THF complex to form a diastereomer mixture of 1-azaadamantan-4-ol N-borane complex; (2) Coupling resulting product with 4-chlorobenzoic acid; (3) Separating (4s) isomer by column chromatography (silica gel, using 3:1 hexanes-EtOAc), followed by removing 4-chlorobenzoic acid moiety with NaOH; (4) Removing BH₃ group with HCl giving (4s)-1-azaadamantan-4-ol in free base form; and (5) Converting free base into HBr salt by treating with HBr in dioxane. Resulting (4s)-1-azaadamantan-4-ol HBr salt is an intermediate to ester-linked azaadamantane derivatives useful for treating diminished CNS function associated with traumatic brain injury or treating inflammatory pain.

U.S. Pat. No. 7,902,222, published 30 Jul. 2009, shows synthesis of 2-bromo-5-phenyl-1,3,4-thiadiazole from 2-amino-5-phenyl-1,3,4-thiadiazole using MeCN, CuBr₂ and iso-amyl nitrite. Resulting compound is an intermediate to compounds useful for treating inflammation and rheumatoid arthritis.

SUMMARY OF INVENTION

A process for preparing azaadamantane derivatives and intermediates obtained by such process are described. More particularly, azaadamantane formate ester intermediate is described. Additionally, a process for preparing azaadamantane formate ester intermediate is described. A process for preparing 1-azaadamantan-4-ol from azaadamantane formate ester is also described. Furthermore, a process for preparing (4s)-4-(5-phenyl-[1,3,4]thiadiazol-2-yloxy)-1-azatricyclo[3.3.1.1$^{3,7}$]-decane, or a salt thereof, is described.

In another aspect, a compound of Formula (I) is described:

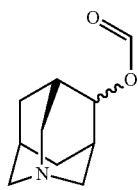

(I)

In another aspect, a process for preparing a compound, or salt of a compound, or solvate of a compound, of Formula (I) is described, comprising contacting (E)-N-benzylidene-1-(cyclohex-3-en-1-yl)methanamine with an aldehyde, or with an acetal, or with a hemiacetal, in presence of formic acid and a reaction medium to form a compound of Formula (I).

In another aspect, a process for preparing a compound, or salt of a compound, or solvate of a compound, of Formula (II) is described:

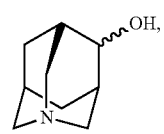

(II)

comprising contacting a compound of Formula (I) with a hydrolyzing agent.

In another aspect, a process for preparing a compound of Formula (II) is described, comprising: (a) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); and (b) contacting a compound of Formula (I) with a hydrolyzing agent.

In another aspect, a process for preparing a compound of Formula (II), is described, comprising: (a) contacting (E)-N-(cyclohex-3-en-1-ylmethylene)-1-phenylmethanamine with an isomerizing agent to form (E)-N-benzylidene-1-(cyclohex-3-en-1-yl)methanamine; (b) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); and (c) contacting a compound of Formula (I) with a hydrolyzing agent.

In another aspect, a process for preparing a compound of Formula (II) is described, comprising: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with an isomerizing agent to form (E)-N-benzylidene-1-(cyclohex-3-en-1-yl)methanamine; (c) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); and (d) contacting a compound of Formula (I) with a hydrolyzing agent.

More specifically, a compound, which is (4s)-1-azaadamantane-4-yl formate ester is described. A process for preparing the (4s)-azaadamantane-4-yl formate ester is also described. Furthermore, a process is described, comprising step of hydrolyzing (4s)-1-azaadamantane-4-yl formate ester to form (4s)-1-azaadamantan-4-ol HBr salt.

In another aspect, a process for preparing a salt of 2-amino-5-phenyl-1,3,4-thiadiazole is described, the process comprising step of contacting aminothiourea and benzoic acid in presence of polyphosphoric acid.

In another aspect, a process for preparing 2-bromo-5-phenyl-1,3,4-thiadiazole, or salt or solvate thereof, is described, the process comprising step of contacting a 2-amino-5-phenyl-1,3,4-thiadiazole salt, a Cu(II)halide and an alkyl-nitrite, in presence of a polar aprotic solvent.

In another aspect, a process for preparing 2-bromo-5-phenyl-1,3,4-thiadiazole, or salt or solvate thereof, is described, the process comprising steps of: (a) contacting aminothiourea and benzoic acid in presence of polyphosphoric acid to form a salt of 5-amino-1,3,4-thiadiazole; and (b) contacting the 2-amino-5-phenyl-1,3,4-thiadiazole salt, a Cu(II)halide and an alkyl-nitrite in presence of a polar aprotic solvent.

In another aspect, a process for preparing a compound, or a salt of a compound, or a solvate thereof, of Formula (III) is described

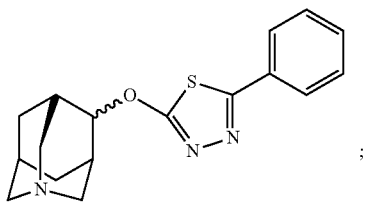
(III)

the process comprising step of contacting a compound, or a salt of a compound, or a solvate of a compound, of Formula (II)

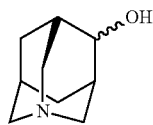
(II)

with 2-bromo-5-phenyl-1,3,4-thiadiazole, in presence of a metal (alkylsilyl)amide and a reaction medium, to form a reaction mixture, and optionally contacting the reaction mixture with citric acid.

In another aspect, a process for preparing a compound, a salt of a compound, or a solvate of a compound thereof, of Formula (III) is described, process comprising steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with an isomerizing agent to form (E)-N-benzylidene-1-(cyclohex-3-en-1-yl)methanamine; (c) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); (d) contacting a compound of Formula (I) with a hydrolyzing agent in a reaction medium to form a compound, or a salt of a compound, of Formula (II); (e) contacting aminothiourea and benzoic acid in presence of polyphosphoric acid to form a 2-amino-5-phenyl-1,3,4-thiadiazole salt; (f) contacting the 2-amino-5-phenyl-1,3,4-thiadiazole salt, a Cu(II)halide and an alkyl-nitrite in presence of a polar aprotic solvent to form 2-bromo-5-phenyl-1,3,4-thiadiazole; and (g) contacting a compound of Formula (II) with 2-bromo-5-phenyl-1,3,4-thiadiazole, in presence of a metal (alkylsilyl)amide and a reaction medium, to form a reaction mixture, and optionally contacting the reaction mixture with citric acid.

DETAILED DESCRIPTION OF THE INVENTION

Definition of Terms

The term "pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals or in humans.

A "salt", which may include a pharmaceutically-acceptable salt, is an ionic compound resulting from the neutralization reaction of an acid and a base or a salt resulting from addition of an organic or inorganic acid. Examples of suitable inorganic acids include hydrochloric acid, hydrobromic acid, hydriodic acid, sulfuric acid, nitric acid and phosphoric acid (including, $H_3PO_4$, $H_2PO_4^-$ and $HPO_4^{2-}$). Examples of suitable organic acids include acetic, adipic, alginic, aspartic, benzenesulfonic (or besylate), benzoic, butyric, camphoric, camphorsulfonic, carbonic, cinnamic, citric (including, for example, mono- and dihydrogen citrate), cyclopentanepropionic, digluconic, ethanesulfonic, fumaric, glucoheptonic, gluconic, glutamic, glycerophosphoric, glycolic, heptanoic, hexanoic, hydroxynaphthoic, lactic, lauryl-sulfuric, maleic (or maleate), malic, malonic, mandelic, methanesulfonic (or mesylate), nicotinic, o-(4-hydroxy-benzoyl)-benzoic, oxalic, pamoic, p-chlorobenzenesulfonic, pectinic, persulfuric, picric, pivalic, propionic, propionic, p-toluenesulfonic, pyruvic, salicylic, stearic, succinic, tartaric (including L-tartrate), tertiary butylacetic, thiocyanic, trimethylacetic, undecanoic, muconic, 1,2-ethanedisulfonic, 2-hydroxyethane-sulfonic, 2-naphthalenesulfonic, 3-phenylpropionic, 3-phenylpropionic, 4,4'-methylenebis(3-hydroxy-2-naphthoic) or 4-methyl-bicyclo[2.2.2]oct-2-ene1-carboxylic acid. The term "salt" embraces metal salts formed with, for example, sodium, potassium, calcium, magnesium, aluminum, iron or zinc ions; or amine salts formed with ammonia or organic nitrogenous bases (e.g., cytosine, thymine, uracil and guanine).

A compound described herein can exist in tautomeric, geometric or stereoisomeric (including atropisomers) forms. Also embraced is an ester, metabolite, oxime, prodrug, onium, hydrate, solvate or N-oxide of a compound of Formula (I), (II), (III) or (IV). The present invention embraces all compounds, including E- and Z-geometric isomers, R- and S-enantiomers, diastereomers, d-isomers, l-isomers, atropisomers, mixtures of isomers and racemates thereof.

The term "solvate" denotes a complex of molecules or ions with those of a compound of Formula (I), (II), (III) or (IV). The term "solvate" embraces the term "hydrate".

The term "hydrate" denotes a compound of Formula (I), (II), (III) or (IV) complexed with water (e.g., monohydrate or dihydrate).

The term "contacting" means that a compound used in a process described herein is provided so that the compound is capable of making physical contact with another molecule, reagent, substance and/or solvent.

The term "in presence of" or "in the presence of" a particular solvent (or reactant) is meant to include a single phase (e.g., in solution) and a multi-phase (e.g., suspension or multi-phase immiscible system) reaction system.

The term "reaction medium" refers to a substance (e.g., water) in which a reactant, product and/or solvent may be present. Reaction medium need not bring about dissolution of reactant or product. "Medium" embraces the term "mixture." In some instances, formic acid can be the reaction medium, or both the reaction medium and a reactant.

The term "mixture" embraces, for example, suspension, solution, colloid, dispersion and/or multiphase immiscible system.

An "isomerizing agent" is capable of converting a compound into a corresponding isomer. More specifically, an isomerizing agent is capable of catalyzing a 1,3-proton shift in an imine, for example:

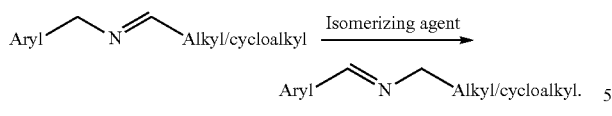

Isomerizing agents include, for example, strong, non-nucleophilic bases (e.g., potassium tert-butoxide, sodium hydride, sodium amide, DBU (1,8-Diazabicyclo[5.4.0]undec-7-ene) and NaN(TMS)$_2$). In some instances, the isomerizing agent may be present in a catalytic amount, for example, about 10 mol %, or ranging from about 0.05 to about 0.2 molar equivalents, of isomerizing agent to starting material.

"Condensing" refers to a chemical reaction in which two molecules combine together to form a different chemical entity, typically generating a water molecule as a by-product.

A "hydrolyzing agent" is capable of cleaving a chemical bond. For example, a hydrolyzing agent can cleave an ester to form an alcohol and acid. Hydrolyzing agents include, for example, HCl, HBr and HI.

The terms "substituent," "radical," "group," "moiety" and "fragment" may be used interchangeably.

Singular forms "a" and "an" may include plural reference unless the context clearly dictates otherwise.

The number of carbon atoms in a substituent can be indicated by the prefix "$C_{A-B}$" where A is the minimum and B is the maximum number of carbon atoms in the substituent.

The term "alkyl" denotes a linear or branched acyclic alkyl radical containing from 1 to about 15 carbon atoms. In some embodiments, alkyl is a $C_{1-10}$alkyl, $C_{1-6}$alkyl or $C_{1-3}$alkyl radical. Examples of alkyl include, but are not limited to, methyl, ethyl, propyl, isopropyl, butyl, isobutyl, tert-butyl, sec-butyl, pentan-3-yl and the like.

The term "alkyl-nitrite" is

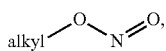

where alkyl is as defined herein. Examples of alkyl-nitrite include iso-amyl-nitrite (also termed nitramyl, (3-methylbutyl)nitrite or 3-methyl-1-nitrosooxybutane), ethyl-nitrite and propyl-nitrite.

The term "nitrite" embraces a radical having a formula of

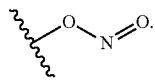 [SMILES: *ON=O]

The term "alkylsilyl" embraces at least one alkyl radical attached to a parent molecular scaffold through a silicon atom. An example of alkyl-silyl is bis(trimethylsilyl).

The term "ether" embraces a radical having a formula of $R^4$—O—$R^5$, where $R^4$ and $R^5$ are each independently alkyl, or $R^4$ and $R^5$ may be taken together to form a cyclic ether. Examples of ether include diethyl ether and tetrahydrofuran.

The term "halide" embraces a binary compound where at least one component is a fluoro, chloro, bromo or an iodo radical.

The term "acetal" is

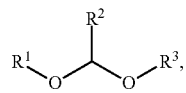

where $R^1$ and $R^3$ may be, for example, alkyl (e.g., methyl, ethyl or propyl), or $R^1$ and $R^3$ may be taken together to form cyclic five or six membered heterocycloalkyl

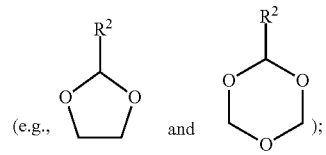

and $R^2$ may be, for example, hydrogen, alkyl, aminoalkyl, or aralkyl. Examples of acetal include, 1,3,5-trioxane; 1,1-diethoxyethane; 1,1-dimethoxyethane; dimethoxymethane; (2,2-dimethoxyethyl)benzene; and 2-methyl-1,3-dioxolane.

The term "hemiacetal" is

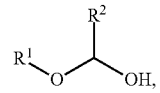

where $R^1$ may be, for example, alkyl (e.g., methyl, ethyl or propyl) HO(CH$_2$O)$_n$—, where n is greater than 8; and where $R^2$ may be, for example, hydrogen, alkyl, aminoalkyl or aralkyl. An example of hemiacetal is paraformaldehyde.

The term "paraformaldehyde" refers to a polymer having formula of HO(CH$_2$O)$_n$H, where n is between about 8 and about 100, having a molecular weight of 30.03 (based on formaldehyde monomer). Although not in alignment with IUPAC nomenclature rules, paraformaldehyde is sometimes referred to as "polyacetal." Furthermore, the term "polyoxymethylene" may embrace paraformaldehyde or polyacetal.

The term "aldehyde" embraces a compound having a —C(O)H moiety, where C(O) is a carbonyl group. Examples of aldehyde include formaldehyde, acetaldehyde, propionaldehyde and benzaldehyde.

In an aqueous solution, paraformaldehyde can convert to formaldehyde and vice versa. Formaldehyde (gas at STP) readily dissolves in water to form methylene hydrate (HO—CH$_2$—OH). Methylene hydrate molecules can further react with each other to form polymers. Generally, a methylene hydrate polymer in solid form, having greater than 8 repeat units, is termed paraformaldehyde. Paraformaldehyde can re-dissolve in water to form formaldehyde. (Renshaw, S., Immunochemical staining techniques, *Immunohistochemistry*. 1 ed. Bloxham: Scion Publishing Limited; 2007:48-50). In aqueous solutions, methanol is added as a stabilizing agent to prevent polymerization of formaldehyde to paraformaldehyde. Formalin is a commercial grade solution of stabilized formaldehyde, comprising 37% formaldehyde and 10-15% MeOH. (See Sigma Aldrich MSDS).

The term "polyphosphoric acid" embraces a phosphoric acid having a formula of $H_{n+2}P_nO_{3n+1}$. Examples of polyphosphoric acid include $H_4P_2O_7$ (pyrophosphoric acid or diphosphoric acid) and $H_5P_3O_{10}$ (triphosphoric acid).

The term "nitrile" embraces a molecule comprising a R—CN moiety, wherein R may be, for example, alkyl or aryl. Examples of nitrile include acetonitrile and benzonitrile.

The term "formate ester" denotes an aldehyde moiety attached to a parent molecular scaffold through an oxygen atom.

The term "aryl" embraces a cyclized aromatic hydrocarbon radical. Aryl may be a monocyclic, bicyclic or tricyclic ring system. Aryl may be attached to cycloalkyl, aryl or heterocyclyl in a fused or pendant manner. Examples of aryl include phenyl and naphthyl.

The term "heterocyclyl" embraces a radical composed of a monocyclic, bicyclic or tricyclic cyclized ring system having from 3 to about 15 ring members selected from carbon, nitrogen, sulfur and oxygen, wherein at least one ring member is a heteroatom. Heterocyclyl embraces a fully saturated (e.g., heterocycloalkyl), partially saturated (e.g., heterocycloalkenyl) and a fully unsaturated radical (e.g., heteroaryl). Heterocyclyl may be fused or attached in a pendant manner to an additional heterocyclyl, aryl or cycloalkyl radical. Heterocyclyl embraces combinations of different heteroatoms within the same cyclized ring system.

The term "aminoalkyl" embraces a primary amino substituted alkyl radical (e.g., $NH_2$-alkyl-molecular scaffold).

The term "alcohol" embraces alkyl substituted with at least one —OH radical. Examples of alcohol include methanol, propanol, ethanol and butanol.

The term "metal (alkylsilyl)amide" embraces a compound comprising a metal cation and an (alkylsilyl)amide anion (e.g., bis(trimethylsilyl)amide). Metal (alkylsilyl)amide embraces a compound having a discrete (alkylsilyl)amide anion as well as a compound having an (alkylsilyl)amide group with partial anionic character bound or coordinated to a metal atom having partial cationic character. Examples of suitable metals include alkali metals, including, lithium, sodium and potassium. An example of a sodium (alkylsilyl)amide is sodium bis(trimethylsilyl)amide (i.e., $NaN(TMS)_2$ or NaHMDS).

The term "polar aprotic solvent" embraces a solvent not capable of donating a hydrogen atom and having a dipole moment ranging from about 1.75 to about 4.0. Examples of a polar aprotic solvents include THF, EtOAc, acetone, DMF, MeCN and DMSO.

The term "polar protic solvent" embraces a solvent capable of donating a hydrogen atom and having a dipole moment ranging from about 1.4 to about 3.6. Examples of polar protic solvents include formic acid, n-butanol, IPA, nitromethane, EtOH, MeOH, acetic acid and water.

The term "or solvate thereof" may embrace both a solvate of a compound of Formula (I), (II), (III) or (IV) and a solvate of a salt of a compound of Formula (I), (II), (III) or (IV), e.g., a monohydrate of a citrate salt of a Compound of Formula (III).

Table 1 shows IUPAC nomenclature, abbreviations as used herein and corresponding molecular structures.

TABLE 1

| IUPAC Name | Abbreviation | Structure |
|---|---|---|
| cyclohex-3-enecarbaldehyde or 3-cyclohexene-1-carboxaldehyde | — | 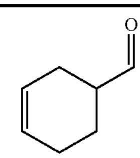 |
| 1-Phenylmethanamine | Benzylamine | 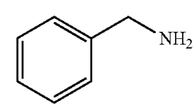 |
| (E)-N-(cyclohex-3-en-1-ylmethylene)-1-phenylmethanamine | Aldimine | 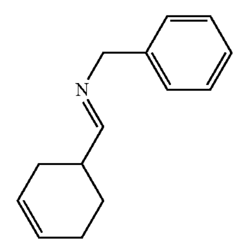 [SMILES: C1=CCC(/C=N/Cc2ccccc2)CC1] |
| (E)-N-benzylidene-1-(cyclohex-3-en-1-yl)methanamine | Isomerized Imine | 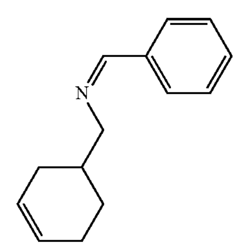 [SMILES: C1=CCC(C/N=C\c2ccccc2)CC1] |
| (3R,4s,5S,7s)-1-azaadamantan-4-yl formate | Azaadamantane formate ester or (4s)-azaadamantan-4-yl formate ester | |

TABLE 1-continued

| IUPAC Name | Abbreviation | Structure |
| --- | --- | --- |
| (3R,4s,5S,7s)-1-azaadamantan-4-ol | (4s)-Azaadamantanol or (4s)-Azaadamantan-4-ol | 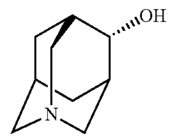 |
| (3R,4r,5S,7s)-1-azaadamantan-4-ol | (4r)-Azaadamantanol | 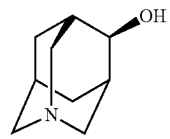 |
| (3R,4s,5S,7s)-1-azaadamantan-4-ol + (3R,4r,5S,7s)-1-azaadamantan-4-ol | Diastereomer mixture of (4s) and (4r) isomers | 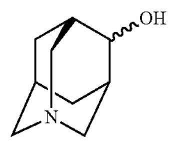 |
| Sodium bis(trimethylsilyl)amide | NaN(TMS)2 | 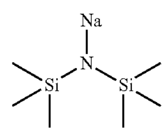 |
| 5-phenyl-1,3,4-thiadiazol-2-amine phosphate salt | — | 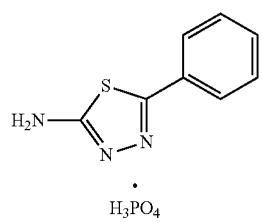 |
| 2-bromo-5-phenyl-1,3,4-thiadiazole | — | 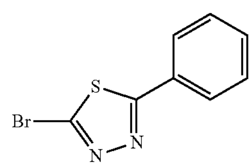 [SMILES: Brc1nnc(-c2ccccc2)s1] |
| 2-hydroxypropane-1,2,3-tricarboxylic acid | Citric Acid | 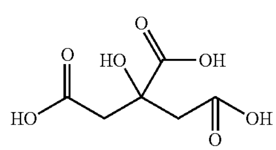 [SMILES: O=C(O)CC(O)(CC(=O)O)C(=O)O] |
| (4s)-4-(5-Phenyl-1,3,4-thiadiazol-2-yloxy)-1-azatricyclo[3.3.1.1$^{3,7}$]-decane or 2-((3R,4s,5S,7s)-1-azaadamantan-4-yloxy)-5-phenyl-1,3,4-thiadiazole | — | |
| (4s)-4-(5-Phenyl-1,3,4-thiadiazol-2-yloxy)-1-azatricyclo[3.3.1.1$^{3,7}$]-decane dihydrogen citrate | Example 7 | 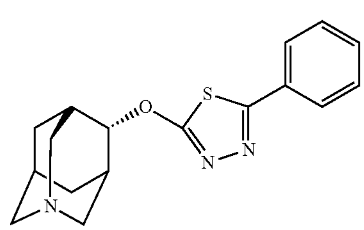 |

TABLE 1-continued

| IUPAC Name | Abbreviation | Structure |
|---|---|---|
| | | 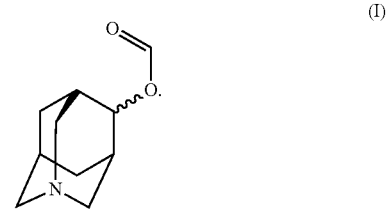 |

List of Abbreviations:
ACN acetonitrile
Boc tert-butyloxycarbonyl
Bu butyl
Bpy 2,2'-bipyridine
DCI dicyclohexylcarbodiimide
DCM dichloromethane or methylenechloride
DIPEA diisopropylethylamine
DMAP 4-dimethylaminopyridine or N,N-dimethylaminopyridine
DME 1,2-dimethoxyethane
DMF N,N-dimethylformamide
DMSO dimethylsulfoxide
$CuBr_2$ copper(II)bromide
EDAC N-(3-dimethylaminopropyl)-N'-ethylcarbodiimide hydrochloride
eq. equivalents
Et ethyl
EtOAC ethyl acetate
EtOH ethanol
HPLC high pressure liquid chromatography
h hour(s)
IPA isopropyl alcohol
$K_2CO_3$ potassium carbonate
KOtBu potassium tert-butoxide
LAH lithium aluminum hydride
LC/MS liquid chromatography mass spectrometry
LC/MS/MS liquid chromatography tandem mass spectrometry
mCPBA m-chloroperbenzoic acid
Me methyl
MeCN acetonitrile
MeOH methanol
$MgSO_4$ magnesium sulfate
mL milliliter
mmol millimole
NaH sodium hydride
$NaN(TMS)_2$ sodium bis(trimethylsilyl)amide
NMR nuclear magnetic resonance
Pd/C palladium on carbon
Ph phenyl
PPA polyphosphoric acid
TEA triethylamine
TFA trifluoroacetic acid
THF tetrahydrofuran
TOSMIC toluenesulfonylmethyl isocyanide
TSA p-toluenesulfonic acid.

In one aspect, a process is described for preparing a compound, or salt of a compound, or solvate of a compound, of Formula (I):

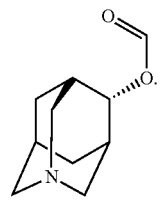

(I)

The process comprises a step of contacting (E)-N-benzylidene-1-(cyclohex-3-en-1-yl)methanamine with an aldehyde, or with an acetal, or with a hemiacetal, in presence of formic acid and a reaction medium. In another aspect, the compound of Formula (I) is

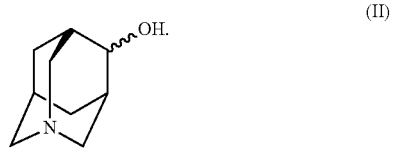

In another aspect, the aldehyde is formaldehyde. In another aspect, the hemiacetal is paraformaldehyde. In another aspect, the paraformaldehyde is present in an amount ranging from about 2.0 molar equivalents to about 5.0 molar equivalents of paraformaldehyde to (E)-N-benzylidene-1-(cyclohex-3-en-1-yl)methanamine. In another aspect, the reaction medium comprises water present in an amount ranging from about 0.1% to about 6.5% of the reaction medium.

In a second, a process is described for preparing a compound, or salt of a compound, or solvate of a compound, of Formula (II):

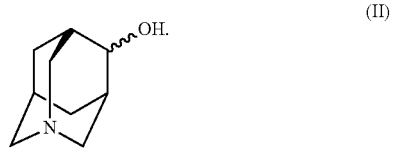

(II)

The process comprises a step of contacting a compound of Formula (I), with a hydrolyzing agent in a reaction medium. In another aspect, the compound of Formula (I) is

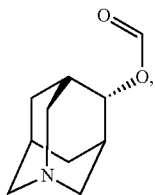

the hydrolyzing agent in a reaction medium is an acid solution and the salt of a compound of Formula (II) is an inorganic salt. In another aspect, the acid solution is a hydrogen halide solution and the inorganic salt is an acid addition salt. In another aspect, the salt of a compound of Formula (II) is

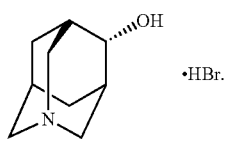

In another aspect, the hydrogen halide solution is a hydrogen bromide solution. In another aspect, the hydrogen bromide solution is an aqueous solution of hydrogen bromide comprising about 43% to about 53% w/w of hydrogen bromide. In another aspect, the about 43% to about 53% w/w aqueous solution of hydrogen bromide is present in an amount ranging from about 1.0 molar equivalent to about 2.0 molar equivalents of the about 43% to about 53% w/w aqueous solution of hydrogen bromide to a compound of Formula (I).

In a third aspect, a process is described for preparing a compound, or salt of a compound, or solvate of a compound, of Formula (II), the process comprises steps of: (a) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); and (b) contacting a compound of Formula (I) with a hydrolyzing agent in a reaction medium. In another aspect, the compound of Formula (I) is

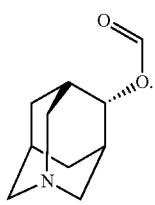

In another aspect, the aldehyde is formaldehyde. In another aspect, the hemiacetal is paraformaldehyde. In another aspect, the paraformaldehyde is present in an amount ranging from about 2.0 molar equivalents to about 5.0 molar equivalents of paraformaldehyde to (E)-N-benzylidene-1-(cyclohex-3-en-1-yl)methanamine. In another aspect, the reaction medium comprises water present in an amount ranging from about 0.1% to about 6.5% of the reaction medium. In another aspect, the hydrolyzing agent in a reaction medium is an acid solution and the salt of a compound of Formula (II) is an inorganic salt. In another aspect, the acid solution is a hydrogen halide solution and the inorganic salt is an acid addition salt. In another aspect, the salt of a compound of Formula (II) is

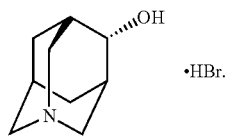

In another aspect, the hydrogen halide solution is a hydrogen bromide solution. In another aspect, the hydrogen bromide solution is an aqueous solution of hydrogen bromide comprising about 43% to about 53% w/w of hydrogen bromide. In another aspect, the about 43% to about 53% w/w aqueous solution of hydrogen bromide is present in an amount ranging from about 1.0 molar equivalent to about 2.0 molar equivalents of the about 43% to about 53% w/w aqueous solution of hydrogen bromide to a compound of Formula (I).

In a fourth aspect, a process is described for preparing a compound, or salt of a compound, or solvate of a compound, of Formula (II), the process comprises steps of: (a) contacting (E)-N-(cyclohex-3-en-1-ylmethylene)-1-phenylmethanamine with an isomerizing agent to form (E)-N-benzylidene-1-(cyclohex-3-en-1-yl)methanamine; (b) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); and (c) contacting a compound of Formula (I) with a hydrolyzing agent in a reaction medium. In another aspect, the compound of Formula (I) is

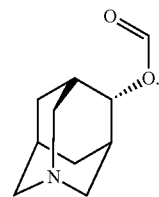

In another aspect, the isomerizing agent is potassium tert-butoxide. In another aspect, the potassium tert-butoxide is present in an amount ranging from about 0.05 molar equivalents to about 3.0 molar equivalents of potassium tert-butoxide to (E)-N-(cyclohex-3-en-1-ylmethylene)-1-phenylmethanamine. In another aspect, the potassium tert-butoxide is present in an amount ranging from about 0.05 molar equivalents to about 0.2 molar equivalents of potassium tert-butoxide to (E)-N-(cyclohex-3-en-1-ylmethylene)-1-phenylmethanamine. In another aspect, the aldehyde is formaldehyde. In another aspect, the hemiacetal is paraformaldehyde. In another aspect, the paraformaldehyde is present in an amount ranging from about 2.0 molar equivalents to about 5.0 molar equivalents of paraformaldehyde to (E)-N-benzylidene-1-(cyclohex-3-en-1-yl)methanamine. In another aspect, the reaction medium comprises water present in an amount ranging from about 0.1% to about 6.5% of the reaction medium. In another aspect, the hydrolyzing agent in a reaction medium is an acid solution and the salt of a compound of Formula (II) is an inorganic salt. In another aspect, the acid solution is a hydrogen halide solution and the inorganic salt is an acid addition salt. In another aspect, the salt of a compound of Formula (II)

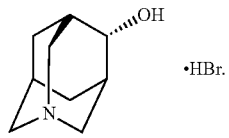

In another aspect, the hydrogen halide solution is a hydrogen bromide solution. In another aspect, the hydrogen bromide solution is an aqueous solution of hydrogen bromide comprising about 43% to about 53% w/w of hydrogen bromide. In another aspect, the about 43% to about 53% w/w aqueous solution of hydrogen bromide is present in an amount ranging from about 1.0 molar equivalent to about 2.0 molar equivalents of the about 43% to about 53% w/w aqueous solution of hydrogen bromide to a compound of Formula (I).

In a fifth aspect, a process is described for preparing a compound, or salt of a compound, or solvate of a compound, of Formula (II), the process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with an isomerizing agent to form (E)-N-benzylidene-1-(cyclohex-3-en-1-yl)methanamine; (c) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); and (d) contacting a compound of Formula (I) with a hydrolyzing agent in a reaction medium. In another aspect, the compound of Formula (I) is

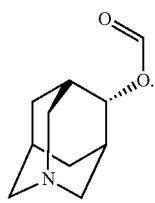

In another aspect, the isomerizing agent is potassium tert-butoxide. In another aspect, the potassium tert-butoxide is present in an amount ranging from about 0.05 molar equivalents to about 3.0 molar equivalents of potassium tert-butoxide to (E)-N-(cyclohex-3-en-1-ylmethylene)-1-phenylmethanamine. In another aspect, the potassium tert-butoxide is present in an amount ranging from about 0.05 molar equivalents to about 0.2 molar equivalents of potassium tert-butoxide to (E)-N-(cyclohex-3-en-1-ylmethylene)-1-phenylmethanamine. In another aspect, the aldehyde is formaldehyde. In another aspect, the hemiacetal is paraformaldehyde. In another aspect, the paraformaldehyde is present in an amount ranging from about 2.0 molar equivalent to about 5.0 molar equivalents of paraformaldehyde to (E)-N-benzylidene-1-(cyclohex-3-en-1-yl)methanamine. In another aspect, the reaction medium comprises water present in an amount ranging from about 0.1% to about 6.5% of the reaction medium. In another aspect, the hydrolyzing agent in a reaction medium is an acid solution and the salt of a compound of Formula (II) is an inorganic salt. In another aspect, the acid solution is a hydrogen halide solution and the inorganic salt is an acid addition salt. In another aspect, the salt of a compound of Formula (II) is

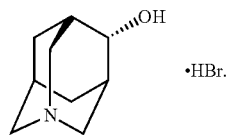

In another aspect, the hydrogen halide solution is a hydrogen bromide solution. In another aspect, the hydrogen bromide solution is an aqueous solution of hydrogen bromide comprising about 43% to about 53% w/w of hydrogen bromide. In another aspect, the about 43% to about 53% w/w aqueous solution of hydrogen bromide is present in an amount ranging from about 1.0 molar equivalent to about 2.0 molar equivalents of the about 43% to about 53% w/w aqueous solution of hydrogen bromide to a compound of Formula (I).

In a sixth aspect, a compound, or a salt of a compound, or solvate of a compound, is described which is

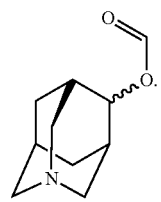

In another aspect, a compound is described which is (3R,4s,5S,7s)-1-azaadamantan-4-yl formate. In another aspect, a compound is described which is (3R,4r,5S,7 s)-1-azaadamantan-4-yl formate.

In a seventh aspect, a process is described that comprises a step of contacting (E)-N-(cyclohex-3-en-1-ylmethylene)-1-phenylmethanamine with an isomerizing agent present in an amount ranging from about 0.05 to 0.2 molar equivalents of the isomerizing agent to the (E)-N-(cyclohex-3-en-1-ylmethylene)-1-phenylmethanamine. In another aspect, the isomerizing agent is potassium tert-butoxide.

In an eighth aspect, a process is described for preparing a 2-amino-5-phenyl-1,3,4-thiadiazole salt. The process comprises a step of contacting aminothiourea and benzoic acid in presence of polyphosphoric acid. In another aspect, the 2-amino-5-phenyl-1,3,4-thiadiazole salt is an inorganic salt. In another aspect, the inorganic salt of 2-amino-5-phenyl-1,3,4-thiadiazole is a phosphate salt. In another aspect, the phosphate salt of 2-amino-5-phenyl-1,3,4-thiadiazole is formed with $H_3PO_4$.

In a ninth aspect, a process is described for preparing 2-bromo-5-phenyl-1,3,4-thiadiazole, or salt or solvate thereof. The process comprises a step of contacting a 2-amino-5-phenyl-1,3,4-thiadiazole salt, a Cu(II)halide and an alkyl-nitrite, in presence of a polar aprotic solvent. In another aspect, the 2-amino-5-phenyl-1,3,4-thiadiazole salt is an inorganic salt, the Cu(II)halide is $CuBr_2$, the alkyl-nitrite is $C_{1-6}$alkyl-nitrite, and the polar aprotic solvent is a nitrile. In another aspect, the inorganic salt of 2-amino-5-phenyl-1,3,4-thiadiazole is a phosphate salt, the $C_{1-6}$alkyl-nitrite is isoamyl nitrite, and the nitrile is acetonitrile. In another aspect, the phosphate salt of 2-amino-5-phenyl-1,3,4-thiadiazole is formed with $H_3PO_4$.

In a tenth aspect, a process is described for preparing 2-bromo-5-phenyl-1,3,4-thiadiazole, or salt or solvate thereof. The process comprises steps of: (a) contacting aminothiourea and benzoic acid in presence of polyphosphoric acid to form a 2-amino-5-phenyl-1,3,4-thiadiazole salt; and (b) contacting the 2-amino-5-phenyl-1,3,4-thiadiazole salt, a Cu(II)halide and an alkyl-nitrite, in presence of a polar aprotic solvent. In another aspect, the 2-amino-5-phenyl-1,3,4-thiadiazole salt is an inorganic salt, the Cu(II)halide is $CuBr_2$, the alkyl-nitrite is $C_{1-6}$alkyl-nitrite, and the polar aprotic solvent is a nitrile. In another aspect, the inorganic salt of 2-amino-5-phenyl-1,3,4-thiadiazole is a phosphate salt, the $C_{1-6}$alkyl-nitrite is iso-amyl nitrite, and the nitrile is acetonitrile. In another aspect, the phosphate salt of 2-amino-5-phenyl-1,3,4-thiadiazole is formed with $H_3PO_4$.

In an eleventh aspect, a process is described for preparing a compound, or a salt of a compound, or a solvate thereof, of Formula (III):

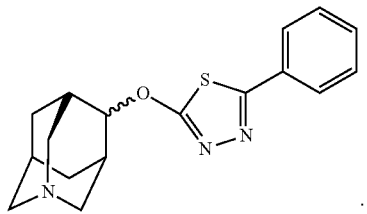

(III)

The process comprises a step of contacting a compound, or a salt of a compound, or a solvate of a compound, of Formula (II) with 2-bromo-5-phenyl-1,3,4-thiadiazole, in presence of a metal (alkylsilyl)amide and a reaction medium, to form a reaction mixture, and optionally contacting the reaction mixture with citric acid. In another aspect, the salt of a compound of Formula (II) is

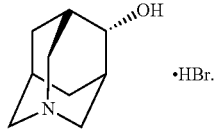

·HBr.

In another aspect, the reaction mixture comprises compound of Formula (II), metal (alkylsilyl)amide and citric acid. In another aspect, the reaction mixture comprises compound of Formula (II) and metal (alkylsilyl)amide to form a reaction mixture, which is contacted with citric acid to form a compound of Formula (IV):

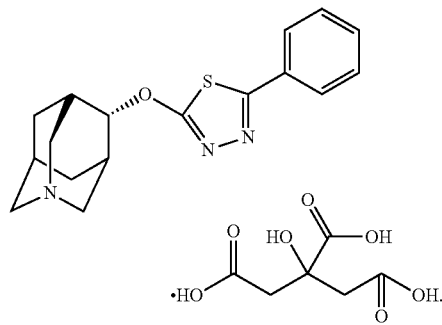

(IV)

In another aspect, the metal (alkylsilyl)amide is an alkali metal bis(trimethylsilyl)amide. In another aspect, the alkali metal bis(trimethylsilyl)amide is sodium bis(trimethylsilyl)amide. In another aspect, the reaction medium comprises a polar aprotic solvent. In another aspect, the polar aprotic solvent is tetrahydrofuran. In another aspect, the reaction medium comprises a polar protic solvent. In another aspect, the polar protic solvent is ethanol.

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with an isomerizing agent to form (E)-N-benzylidene-1-(cyclohex-3-en-1-yl)methanamine; (c) contacting (E)-N-benzylidene-1-(cyclohex-3-en-1-yl)methanamine with an aldehyde, or with an acetal, or with a hemiacetal, in presence of formic acid and a reaction medium to form a compound of Formula (I); (d) contacting a compound of Formula (I) with a hydrolyzing agent in a reaction medium to form a compound, or a salt of a compound, of Formula (II); (e) contacting aminothiourea and benzoic acid in presence of polyphosphoric acid to form a 2-amino-5-phenyl-1,3,4-thiadiazole salt; (f) contacting a 2-amino-5-phenyl-1,3,4-thiadiazole salt, a Cu(II)halide and an alkyl-nitrite, in presence of a polar aprotic solvent to form 2-bromo-5-phenyl-1,3,4-thiadiazole; and (g) contacting a compound of Formula (II) with 2-bromo-5-phenyl-1,3,4-thiadiazole, in presence of a metal (alkylsilyl)amide and a reaction medium, to form a reaction mixture, and optionally contacting the reaction mixture with citric acid. In another aspect, the reaction mixture comprises

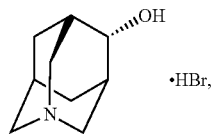

·HBr, a metal (alkylsilyl)amide and citric acid. In another aspect, the reaction mixture

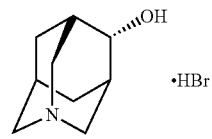

·HBr and a metal (alkylsilyl)amide to form a reaction mixture, which is contacted with citric acid to form a compound of Formula (IV).

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with potassium tert-butoxide to form (E)-N-benzylidene-1-(cyclohex-3-en-1-yl)methanamine; (c) contacting (E)-N-benzylidene-1-(cyclohex-3-en-1-yl)methanamine with paraformaldehyde, in presence of formic acid and a reaction medium to form a compound of Formula (I); (d) contacting a compound of Formula (I) with a hydrolyzing agent in an acid solution to form an inorganic salt of a compound of Formula (II); (e) contacting aminothiourea and benzoic acid in presence of polyphosphoric acid to form a 2-amino-5-phenyl-1,3,4-thiadiazole inorganic salt; (f) contacting a 2-amino-5-phenyl-1,3,4-thiadiazole inorganic salt, $CuBr_2$ and an $C_{1-6}$alkyl-nitrite, in presence of a nitrile to form 2-bromo-5-phenyl-1,3,4-thiadiazole; and (g) contacting a compound of Formula (II) with 2-bromo-5-phenyl-1,3,4-thiadiazole, in presence of an alkali metal bis(trimethylsilyl)amide and a reaction medium, to form a reaction mixture, and optionally contacting the reaction mixture with citric acid. In another aspect, the reaction mixture comprises

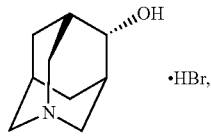

an alkali metal bis(trimethylsilyl)amide and citric acid. In another aspect, the reaction mixture comprises a

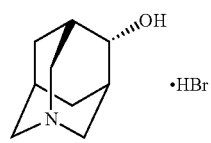

and alkali metal bis(trimethylsilyl)amide to form a reaction mixture, which is contacted with citric acid to form a compound of Formula (IV).

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with potassium tert-butoxide present in an amount ranging from about 0.05 molar equivalents to about 3.0 molar equivalents of potassium tert-butoxide to (E)-N-(cyclohex-3-en-1-ylmethylene)-1-phenylmethanamine to form (E)-N-benzylidene-1-(cyclohex-3-en-1-yl)methanamine; (c) contacting (E)-N-benzylidene-1-(cyclohex-3-en-1-yl)methanamine with paraformaldehyde present in an amount ranging from about 2.0 molar equivalents to about 5.0 molar equivalents of paraformaldehyde to (E)-N-benzylidene-1-(cyclohex-3-en-1-yl)methanamine, in presence of formic acid and a reaction medium to form a compound of Formula (I); (d) contacting a compound of Formula (I) with an a hydrogen halide solution to form an acid addition salt of a compound of Formula (II); (e) contacting aminothiourea and benzoic acid in presence of polyphosphoric acid to form a 2-amino-5-phenyl-1,3,4-thiadiazole phosphate salt; (f) contacting a 2-amino-5-phenyl-1,3,4-thiadiazole salt, $CuBr_2$ and iso-amyl nitrite, in presence of acetonitrile, to form 2-bromo-5-phenyl-1,3,4-thiadiazole; and (g) contacting the acid addition salt of a compound of Formula (II) with 2-bromo-5-phenyl-1,3,4-thiadiazole, in presence of a sodium bis(trimethylsilyl)amide and a reaction medium, to form a reaction mixture, and optionally contacting the reaction mixture with citric acid. In another aspect, the reaction mixture comprises

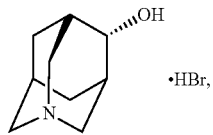

sodium bis(trimethylsilyl)amide and citric acid. In another aspect, the reaction mixture comprises

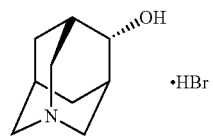

and sodium bis(trimethylsilyl)amide to form a reaction mixture, which is contacted with citric acid to form a compound of Formula (IV).

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with potassium tert-butoxide present in an amount ranging from about 0.05 molar equivalents to about 0.2 molar equivalents of potassium tert-butoxide to (E)-N-(cyclohex-3-en-1-ylmethylene)-1-phenylmethanamine to form (E)-N-benzylidene-1-(cyclohex-3-en-1-yl)methanamine; (c) contacting (E)-N-benzylidene-1-(cyclohex-3-en-1-yl)methanamine with paraformaldehyde present in an amount ranging from about 2.0 molar equivalents to about 5.0 molar equivalents of paraformaldehyde to (E)-N-benzylidene-1-(cyclohex-3-en-1-yl)methanamine, in presence of formic acid and a reaction medium comprising water present in an amount ranging from about 0.1% to about 6.5% of the reaction medium to form a compound of Formula (I); (d) contacting a compound of Formula (I) with an a hydrogen bromide solution and where the inorganic salt of a compound of Formula (II) is an acid addition salt; (e) contacting aminothiourea and benzoic acid in presence of polyphosphoric acid to form a 2-amino-5-phenyl-1,3,4-thiadiazole $H_3PO_4$ salt; (f) contacting 2-amino-5-phenyl-1,3,4-thiadiazole $H_3PO_4$ salt, $CuBr_2$ and iso-amyl nitrite, in presence of acetonitrile, to form 2-bromo-5-phenyl-1,3,4-thiadiazole; and (g) contacting a compound of Formula (II) with 2-bromo-5-phenyl-1,3,4-thiadiazole, in presence of a sodium bis(trimethylsilyl)amide and a polar aprotic solvent, to form a reaction mixture, and optionally contacting the reaction mixture with citric acid. In another aspect, the reaction mixture comprises

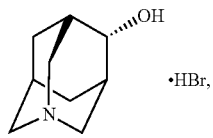

sodium bis(trimethylsilyl)amide and citric acid. In another aspect, the reaction mixture comprises

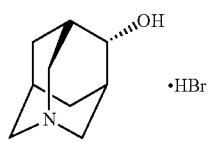

and sodium bis(trimethylsilyl)amide to form a reaction mixture, which is contacted with citric acid to form a compound of Formula (IV).

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with potassium tert-butoxide present in an amount ranging from about 0.05 molar equivalents to about 0.2 molar equivalents of potassium tert-butoxide to (E)-N-(cyclohex-3-en-1-ylmethylene)-1-phenylmethanamine to form (E)-N-benzylidene-1-(cyclohex-3-en-1-yl)methanamine; (c) contacting (E)-N-benzylidene-1-(cyclohex-3-en-1-yl)methanamine with paraformaldehyde present in an amount ranging from about 2.0 molar equivalents to about 5.0 molar equivalents of paraformaldehyde to (E)-N-benzylidene-1-(cyclohex-3-en-1-yl)methanamine, in presence of formic acid and a reaction medium comprising water present in an amount ranging from about 0.1% to about 6.5% of the reaction medium to form a compound of Formula (I); (d) contacting a compound of Formula (I) with a hydrogen bromide solution comprising about 43% to about 53% w/w of hydrogen bromide and where the inorganic salt of a compound of Formula (II) is an HBr salt; (e) contacting aminothiourea and benzoic acid in presence of polyphosphoric acid to form 2-amino-5-phenyl-1,3,4-thiadiazole $H_3PO_4$ salt; (f) contacting 2-amino-5-phenyl-1,3,4-thiadiazole $H_3PO_4$ salt, $CuBr_2$ and iso-amyl nitrite, in presence of a acetonitrile, to form 2-bromo-5-phenyl-1,3,4-thiadiazole; and (g) contacting a compound of Formula (II) with 2-bromo-5-phenyl-1,3,4-thiadiazole, in presence of a sodium bis(trimethylsilyl)amide and tetrahydrofuran, to form a reaction mixture, and optionally contacting the reaction mixture with citric acid. In another aspect, the reaction mixture comprises

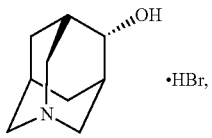

sodium bis(trimethylsilyl)amide and citric acid. In another aspect, the reaction mixture comprises

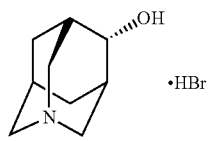

and sodium bis(trimethylsilyl)amide to form a reaction mixture, which is contacted with citric acid to form a compound of Formula (IV).

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with potassium tert-butoxide present in an amount ranging from about 0.05 molar equivalents to about 0.2 molar equivalents of potassium tert-butoxide to (E)-N-(cyclohex-3-en-1-ylmethylene)-1-phenylmethanamine to form (E)-N-benzylidene-1-(cyclohex-3-en-1-yl)methanamine; (c) contacting (E)-N-benzylidene-1-(cyclohex-3-en-1-yl)methanamine with paraformaldehyde present in an amount ranging from about 2.0 molar equivalents to about 5.0 molar equivalents of paraformaldehyde to (E)-N-benzylidene-1-(cyclohex-3-en-1-yl)methanamine, in presence of formic acid and a reaction medium comprising water present in an amount ranging from about 0.1% to about 6.5% of the reaction medium to form a compound of Formula (I); (d) contacting a compound of Formula (I) with a hydrogen bromide solution comprising about 43% to about 53% w/w of hydrogen bromide present in an amount ranging from about 1.0 molar equivalent to about 2.0 molar equivalents of the about 43% to about 53% w/w aqueous solution of hydrogen bromide to a compound of Formula (I) and where the inorganic salt of a compound of Formula (II) is

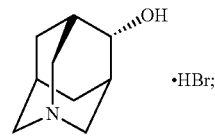

(e) contacting aminothiourea and benzoic acid in presence of polyphosphoric acid to form 2-amino-5-phenyl-1,3,4-thiadiazole $H_3PO_4$ salt; (f) contacting 2-amino-5-phenyl-1,3,4-thiadiazole $H_3PO_4$ salt, $CuBr_2$ and iso-amyl nitrite, in presence of acetonitrile, to form 2-bromo-5-phenyl-1,3,4-thiadiazole; and (g) contacting a compound of Formula (II) with 2-bromo-5-phenyl-1,3,4-thiadiazole, in presence of a sodium bis(trimethylsilyl)amide and a polar protic solvent, to form a reaction mixture, and optionally contacting the reaction mixture with citric acid. In another aspect, the reaction mixture comprises

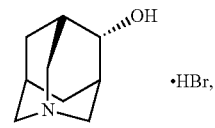

sodium bis(trimethylsilyl)amide and citric acid. In another aspect, the reaction mixture comprises

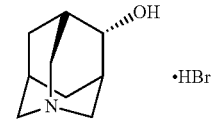

and sodium bis(trimethylsilyl)amide to form a reaction mixture, which is contacted with citric acid to form a compound of Formula (IV).

In another aspect, a process is described for preparing a compound, or a salt of a compound, or a solvate thereof, of Formula (III). The process comprises steps of: (a) condensing benzylamine with cyclohex-3-enecarbaldehyde to form (E)-N-(cyclohex-3-en-1-ylmethylene)-1-phenylmethanamine; (b) contacting (E)-N-(cyclohex-3-en-1-ylmethylene)-1-phenylmethanamine with potassium tert-butoxide present in an amount ranging from about 0.05 molar equivalents to about 0.2 molar equivalents of potassium tert-butoxide to (E)-N-(cyclohex-3-en-1-ylmethylene)-1-phenylmethanamine to form (E)-N-benzylidene-1-(cyclohex-3-en-1-yl)methanamine; (c) contacting (E)-N-benzylidene-1-(cyclohex-3-en-1-yl)methanamine with paraformaldehyde present in an amount ranging from about 2.0 molar equivalents to about 5.0 molar equivalents of paraformaldehyde to (E)-N-benzylidene-1-(cyclohex-3-en-1-yl)methanamine, in presence of formic acid and a reaction medium comprising water present in an amount ranging from about 0.1% to about 6.5% of the reaction medium to form a compound of Formula (I); (d) contacting a compound of Formula (I) with a hydrogen bromide aqueous solution comprising about 43% to about 53% w/w of hydrogen bromide present in an amount ranging from about 1.0 molar equivalent to about 2.0 molar equivalents of the about 43% to about 53% w/w aqueous solution of hydrogen bromide to a compound of Formula (I), the acid addition salt is an HBr salt, and the salt of a compound of Formula (II) is

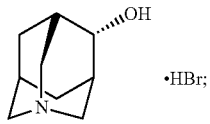

·HBr;

(e) contacting aminothiourea and benzoic acid in presence of polyphosphoric acid to form 2-amino-5-phenyl-1,3,4-thiadiazole $H_3PO_4$ salt; (f) contacting 2-amino-5-phenyl-1,3,4-thiadiazole $H_3PO_4$ salt, $CuBr_2$ and iso-amyl nitrite, in presence of a acetonitrile, to form 2-bromo-5-phenyl-1,3,4-thiadiazole; and (g) contacting a compound of Formula (II) with 2-bromo-5-phenyl-1,3,4-thiadiazole, in presence of sodium bis(trimethylsilyl)amide and ethanol, to form a reaction mixture, and optionally contacting the reaction mixture with citric acid. In another aspect, the reaction mixture comprises

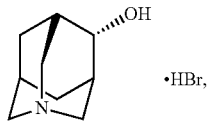

·HBr, sodium bis(trimethylsilyl)amide and citric acid. In another aspect, the reaction mixture comprises

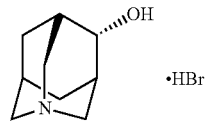

·HBr and sodium bis(trimethylsilyl)amide to form a reaction mixture, which is contacted with citric acid to form a compound of Formula (IV).

Methods for Preparing Compounds of the Invention

Reactions exemplified in schemes below are performed in a solvent appropriate for reagents and materials employed and suitable for transformations thereof.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl and trifluoroacetyl. More particularly, the Boc protecting group may be removed by treatment with an acid such as trifluoroacetic acid or hydrochloric acid. The Cbz and Bn protecting groups may be removed by catalytic hydrogenation.

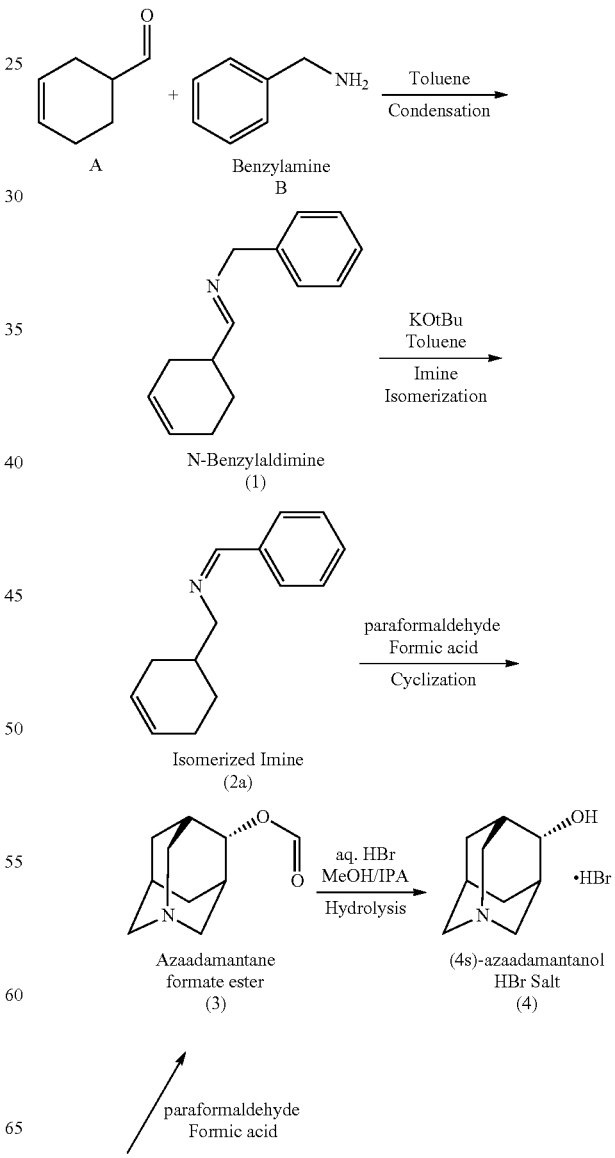

-continued

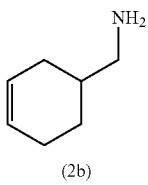

(2b)

As outlined in Scheme 1, Compound (A) (cyclohex-3-enecarbaldehyde, commercially available from Zerenex Molecular Ltd.), stirred overnight in presence of Compound (B) (benzylamine, commercially available from Sigma-Aldrich [100-49-9]), in an aprotic solvent such as, but not limited to, toluene or THF, will provide Compound (1).

Compound (1), in presence of a base such as KOtBu, in an aprotic solvent such as, but not limited to, toluene, is heated to reflux and stirred, providing Compound (2a). A further synthetic description pertaining to the isomerized imine may be found in Kimpe et al., *Tetrahedron*, Vol. 53, No. 31, pg. 10803-10816 (1997). Compound (2a) is carried forward without further purification.

Compound (2a), stirred overnight in presence of an aldehyde such as, but not limited to, paraformaldehyde, in presence of water, and in presence of a substance such as an acid, more specifically formic acid, provides Compound (3). Compound (3) is carried forward without further purification.

Alternatively, Compound (2b), in presence of an aldehyde such as, but not limited to, paraformaldehyde, optionally in presence of water, and in presence of a substance such as an acid, more specifically formic acid, provides Compound (3).

Compound (3), when treated with an acid, for example HBr, in a solvent, for example MeOH and/or IPA, provides Compound (4). The solid is filtered, washed and dried under vacuum to give (4s)-azaadamantan-4-ol HBr salt (4). Compound (4) is used in Scheme 3 without further purification.

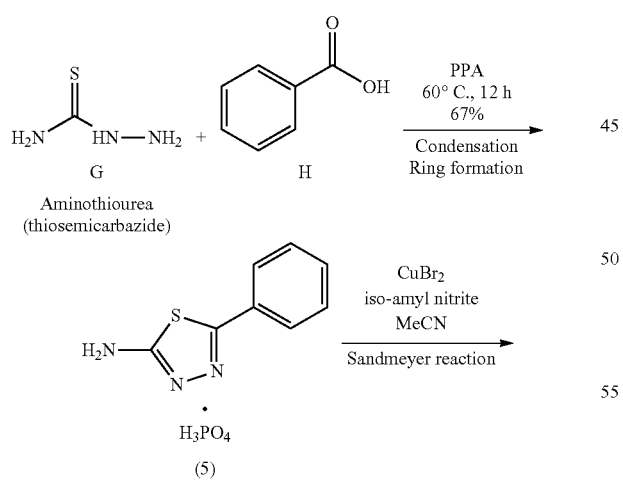

Scheme 2

As outlined in Scheme 2, Compound (G) (commercially available from Sigma-Aldrich [79-19-6]), in presence of Compound (H), in an acidic solvent, for example polyphosphoric acid (PPA), heated for 12 h, will provide Compound (5). Compound (5) is carried forward without further purification.

Compound (5), when treated with a metal catalyst, for example a Cu(II)halide, more specifically $CuBr_2$, in presence of alkyl nitrite, for example iso-amyl nitrite, and in presence of a polar aprotic solvent, for example, a nitrile, even more specifically MeCN, will provide Compound (6). Compound (6) is used in Scheme 3 without further purification.

Scheme 3

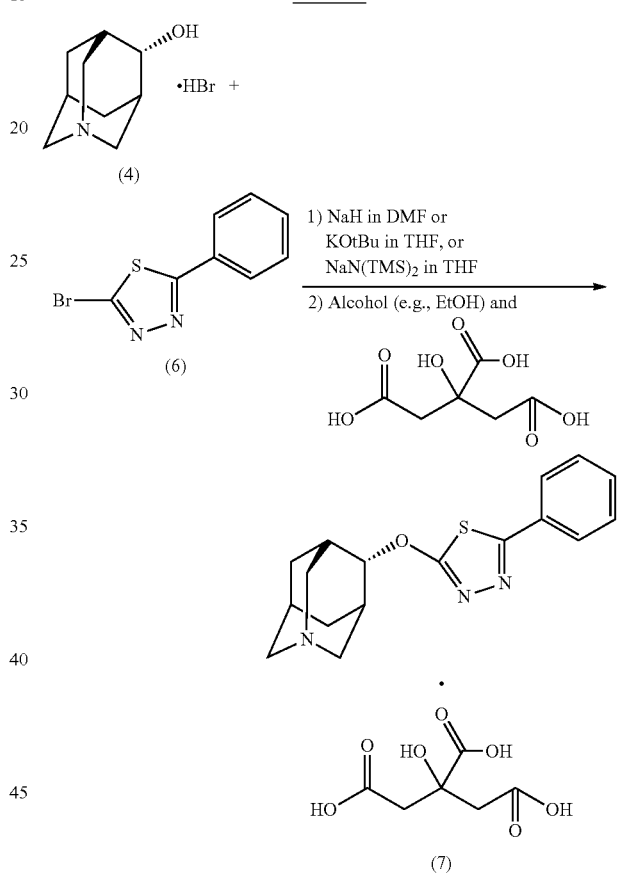

As outlined in Scheme 3, Compound (4), when treated with sodium hydride in DMF, potassium tert-butoxide, potassium bis(trimethylsilylamide), or sodium bis(trimethylsilylamide), in THF or DMSO followed by treatment with 2-bromo-5-phenyl-1,3,4-thiadiazole and citric acid in an alcohol, for example, EtOH, will provide Compound (7).

Example 1

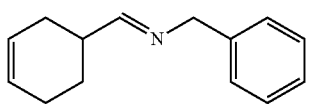

(E)-N-(cyclohex-3-en-1-ylmethylene)-1-phenylmethanamine

To a flask equipped with a Dean-Stark apparatus was added benzylamine (B) (97.3 g, 0.91 mol) and toluene (350 g). The mixture was warmed to 110-115° C. and 3-cyclohexene-1-carboxaldehyde (A) (100 g, 0.91 mol) was added over 1-1.5 h, while azeotropically removing water. After the addition was complete, toluene was distilled (approx. 100 mL) and then the reaction was cooled to 20-30° C. The resulting solution was approximately 40 w/w % (1) in toluene. The solution of (1) in toluene was carried forward without further isolation or purification. Typical assay: 99 area % purity (GC), retention time 15.3 min. $^1$H NMR (400 MHz, CDCl$_3$) δ 7.78-7.75 (1H, m), 7.37-7.32 (2H, m), 7.30-7.26 (3H, m), 5.75-5.73 (2H, m), 4.62 (2H, s), 2.62-2.52 (1H, m), 2.31-2.23 (1H, m), 2.20-2.11 (3H, m), 2.00-1.93 (1H, m), 1.68-1.58 (1H, m).

Example 2

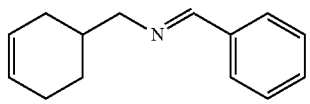

(E)-N-benzylidene-1-(cyclohex-3-en-1-yl)methanamine

To the solution of (1) in toluene (approx. 40 w/w %) was added potassium tert-butoxide (10.2 g, 0.09 mol). The mixture was heated to 80-85° C. for 16 h and subsequently cooled to 20-25° C. Water (17 g) was added and the mixture was stirred at 20-25° C. for 30 min. After settling and separation of the water layer, the toluene layer containing (2) was then concentrated by vacuum distillation. Compound (2) was carried forward without further purification. Typical assay: 96 area % (GC), retention time 15.6 minutes. $^1$H NMR (400 MHz, CDCl$_3$) δ 8.30-8.28 (1H, m), 7.78-7.74 (2H, m), 7.45-7.42 (3H, m), 5.73-5.71 (2H, m), 3.60-3.58 (2H, m), 2.14-2.08 (3H, m), 1.90-1.80 (3H, m), 1.42-1.31 (1H, m).

Example 3

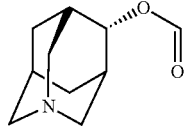

(3R,4s,5S,7s)-1-azaadamantan-4-yl formate

To Compound (2) was added formic acid (1325 g) followed by paraformaldehyde (163 g, 5.4 mol based on formaldehyde monomer molecular weight of 30.03). The mixture was stirred at 40° C. for 6 h. The mixture was concentrated by vacuum distillation to remove formic acid until final volume was approximately 400 mL. In-process sampling typically shows 73 area % Example (3) (RT 12.6 minutes) and complete consumption of (2). Compound (3) was carried forward without further purification. Characterization of (3) was obtained by preparing HBr salt through addition of HBr to a solution of (3) in IPA. The HBr salt was isolated by filtration. $^1$H NMR (400 MHz, DMSO) δ 9.68 (s, 1H), 8.29 (s, 1H), 5.20 (s, 1H), 3.54 (s, 4H), 3.44 (s, 2H), 2.50 (s, 1H), 2.24 (s, 1H), 2.10-1.95 (m, 3H), 1.82 (d, J=12.8 Hz, 2H). LC-MS data: m/z (obs'd)=182.1 [M+1]

Example 4

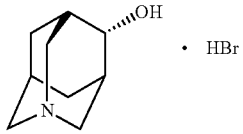

(3R,4s,5S,7s)-1-azaadamantan-4-ol hydrobromide

Methanol (1420 g) was added to (3), followed by addition of aqueous 48% (w/w) hydrobromic acid (230 g) and the mixture was heated to 35° C. for 15 h. The mixture was then concentrated by vacuum distillation. Isopropanol (1860 g) was added and then distilled to a final volume of approx. 1800 mL. After stirring for 1 h at 20° C., (4) was isolated by filtration. The cake was washed with isopropanol, and then dried at 50° C. The final cake weighed 164 g (76% yield). Typical assay=98.3 w/w %, >99.5% purity. $^1$H NMR (400 MHz, DMSO) δ 9.4 (1H, s), 5.25-5.23 (1H, m), 3.96-3.92 (1H, m), 3.49-3.42 (2H, m), 3.40-3.34 (4H, m), 2.16-2.09 (2H, m), 1.96 (3H, s), 1.68-1.62 (2H, m). LC-MS data: m/z (obs'd)=154.2 [M+1].

Example 5

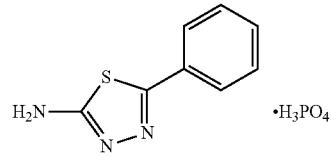

5-Phenyl-1,3,4-thiadiazol-2-amine Phosphate Salt

Benzoic acid (20.0 g, 164 mmol) and thiosemicarbazide (14.93 g, 164 mmol) were ground together in a mortar and pestle then charged in approximately 3-5 g portions over 4 hours to a flask containing polyphosphoric acid (180 g) that had been warmed to 55-60° C. After the addition was complete, the reaction mixture was stirred at 55-60° C. for 14 h. After cooling to 25-30° C., the reaction was carefully quenched with water (300 mL). The quenched slurry was cooled to 0-5° C. and mixed for 3 h and the crude product was isolated by filtration. The crude wet cake was charged back to the original flask and slurried in water (300 mL) at RT for 1 hour. The slurry was filtered, and then the product was slurried in THF (160 mL) at RT for 1 h. The product was isolated by filtration and dried to give 31.6 g (70%) of (5). Typical assay >95 w/w %, >98% purity). ¹H NMR (400 MHz, DMSO) δ 7.77-7.70 (m, 2H), 7.49-7.39 (m, 3H).

Example 6

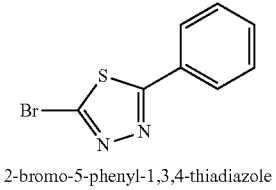 [SMILES: Brc1nnc(-c2ccccc2)s1]

2-bromo-5-phenyl-1,3,4-thiadiazole

A suspension of (5) (10.0 g, 36.3 mmol) in acetonitrile (50 mL) was treated with copper (II) bromide (9.74 g, 43.6 mmol) which was added as a solid in portions over 15 min. at room temperature. After cooling to 0-5° C., iso-amylnitrite was added to the suspension over 90 min. while maintaining the temperature at 0-10° C. The reaction mixture was slowly warmed to room temperature and mixed for 4 h. The reaction mixture was then cooled to 10-15° C. and quenched with water (100 mL). After mixing at 10-15° C. for 1 h, the crude product was filtered and rinsed with cold water (20 mL). The crude solid was suspended in ethyl acetate (120 mL) and after mixing at room temperature for 30 min., the slurry was filtered to remove the solid. The filtrate was washed with 5% aqueous sodium dithionate solution (2×50 mL), then washed with 1.5 N HCl solution (75 mL), and finally washed with water (75 mL). The organic layer was treated with carbon (0.43 g) and mixed at room temperature for 30 min. The mixture was filtered through celite and rinsed with ethyl acetate (10 mL). The filtrate was then concentrated under vacuum to approximately 10 mL and n-heptane (30 mL) was added. The slurry was heated to 55-60° C. to dissolve the solids and the solution was then cooled to 5-10° C. After mixing for 1 h, the slurry was filtered and the product was rinsed with cold n-heptane (5 mL).

The solid was then dissolved in ethyl acetate (50 mL) and carbon (0.43 g) was added to the mixture. After mixing at room temperature for 30 min, the mixture was filtered through celite and rinsed with ethyl acetate (10 mL). The filtrate was then concentrated under vacuum to approximately 10 mL and n-heptane (30 mL) was added. The slurry was heated to 55-60° C. to dissolve the solids and the solution was then cooled to 5-10° C. After mixing for 1 h, the slurry was filtered and the product was rinsed with cold n-heptane (5 mL) then dried under vacuum at 45-50° C. to give (6) as a white solid (4.47 g, 51%). Typical assay >98 w/w %, >99.5% purity). ¹H NMR (400 MHz, CDCL₃) δ 7.95-7.90 (m, 2H), 7.59-7.49 (m, 3H).

Example 7

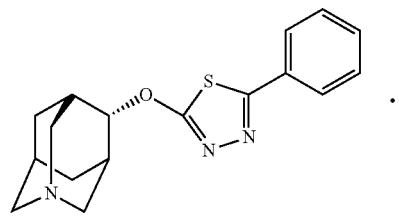

-continued

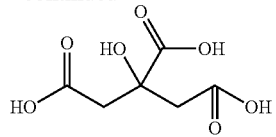

(4s)-4-(5-Phenyl-1,3,4-thiadiazol-2-yloxy)-1-azatricyclo[3.3.1.1³,⁷]-decane Citrate Salt To a 250 mL round bottom flask were charged (4) (4.79 g, 20.5 mmol) and THF (25 mL) and the resulting slurry was mixed under a nitrogen atmosphere. The mixture was cooled to 0-5° C. and then a 1.0M solution of sodium bis(trimethylsilylamide) in THF (40 mL, 40 mmol) was charged. The slurry was warmed to 20-25° C. and stirred for 1 h. The slurry was then cooled to 0-5° C. and a solution of (6) (4.70 g, 39.4 mmol) in THF (14 mL) was charged. The slurry was stirred with cooling for 5-10 minutes after completion of the addition. The slurry was warmed to 20-25° C. for 18 h. In process analysis typically showed less than 1% of (6) remaining.

The mixture was then cooled to 10-15° C. and 10% sodium carbonate (65 mL) was charged. The solution was extracted with ethyl acetate (110 mL). The organic layer was washed successively with 10% potassium carbonate ((40 mL) followed by 7% sodium chloride (40 mL). The ethyl acetate solution was treated with activated carbon (0.93 g), mixed for 10 min and filtered through celite. The celite/carbon filter cake was washed with ethyl acetate (25 mL). The ethyl acetate was concentrated under vacuum to approximately 30 g. Ethanol (35 mL) was charged and the solution was concentrated to approximately 30 g (two times).

To the above mixture was charged ethanol (55 mL) and the batch was heated to 50° C. A solution of citric acid (4.12 g, 21.4 mmol) in ethanol (35 mL) was then added, while maintaining an internal temperature of 45-55° C. The mixture was heated to 60° C. for 1 h, then cooled to 20-25° C. The solids were isolated by filtration, washed with ethanol (32 mL), and vacuum dried at 60-65° C. to yield 9.0 g of (7) (yield 92%). Typically the purity was >99.5%. ¹H NMR (400 MHz, DMSO) δ 7.89-7.79 (m, 2H), 7.58-7.49 (m, 3H), 5.42 (t, J=3.3 Hz, 1H), 3.64-3.44 (m, 4H), 3.40 (s, 2H), 2.58 (d, J=15.1 Hz, 2H), 2.6-2.5 (m, 2H), 2.51 (d, J=15.1 Hz, 2H), 2.12 (d, J=13.0 Hz, 2H), 2.08-1.98 (m, 1H), 1.86 (d, J=12.6 Hz, 2H). LC-MS data: m/z (obs'd)=314.3 [M+1].

Example 8

(4s)-4-(5-Phenyl-1,3,4-thiadiazol-2-yloxy)-1-azatricyclo[3.3.1.1³,⁷]-decane Citrate Monohydrate Seed slurry preparation: A seed slurry was prepared using (4s)-4-(5-phenyl-1,3,4-thiadiazol-2-yloxy)-1-azatricyclo[3.3.1.1³,⁷]-decane dihydrogen citrate monohydrate of (7) (200 mg) in 1.2 g of an 88:12 (w/w) isopropanol/water mixture. Alternately, if monohydrate seeds are not available, 200 mg of the (4s)-4-(5-phenyl-1,3,4-thiadiazol-2-yloxy)-1-azatricyclo[3.3.1.1³,⁷]-decane dihydrogen citrate (7) anhydrate solid can be suspended in approximately 1.0 mL of water. Subsequently, the suspension was sealed with parafilm and stored in a cabinet, protected from light conditions, at ambient conditions for a sufficient time to allow crystallization. Both of the above preparations give adequate seeds for the crystallization. See U.S. Patent Application Publication No. 2012/0245195, published 27 Sep. 2012, for further description pertaining to synthesis of monohydrate citrate salt of (7), the contents of which are incorporated herein by reference.

Crystallization: A 250-mL round bottom flask was charged with (7) (anhydrous form) (10.0 g, 19.8 mmol), water (10.0 g), and isopropanol (31.4 g). The mixture was heated to 75° C. to dissolve the solid. The solution was then cooled to 65° C. over 30 min.

The seed slurry was then added to the bulk solution. The mixture was stirred at 65° C. for 2.5 h and then isopropanol (47.2 g) was added over 4 h. The mixture was held at 65° C. for 30 min. and then cooled to 0° C. over 12 h. The mixture was filtered and the solid was washed with a cold isopropanol/water (44.4 g isopropanol and 3.6 g water). The solid was dried in a vacuum oven at 50° C. for 4 h to afford 10.0 g of (8) as a white solid (97.0 w/w %, 97% yield). Typically the purity was >99.8%. $^1$H NMR (400 MHz, DMSO) δ 7.89-7.79 (m, 2H), 7.58-7.49 (m, 3H), 5.42 (t, J=3.3 Hz, 1H), 3.64-3.44 (m, 4H), 3.40 (s, 2H), 2.58 (d, J=15.1 Hz, 2H), 2.6-2.5 (m, 2H), 2.51 (d, J=15.1 Hz, 2H), 2.12 (d, J=13.0 Hz, 2H), 2.08-1.98 (m, 1H), 1.86 (d, J=12.6 Hz, 2H). LC-MS data: m/z (obs'd)= 314.3 [M+1].

HPLC Conditions:

| Column: Ascentis Express C18, 150 × 4.6 mm, 2.7 micron Mobile phase A = water Mobile phase B = acetonitrile | |
|---|---|
| Time (min) | Gradient (A/B) |
| 0 | 80/20 |
| 10 | 10/90 |
| 14 | 0/100 |
| 14.1 | 80/20 |

Flow rate 1.5 mL/min
210 nm
Column temp 35° C.

GC CHROMATOGRAPHIC CONDITIONS:

| Gas chromatograph with flame ionization detector | |
|---|---|
| Column: | Agilent HP-5, 30 m × 0.32 mm, 0.25 μm film thickness or equivalent |
| Carrier Gas: | Helium |
| Mode: | Constant flow |
| Column flow rate: | 2.0 mL/min. |
| Injection mode: | Split |
| Injection volume: | 1 μL |
| Split ratio: | 10:1 |
| Injector Temperature ° C.: | 200 |
| Detector Temperature ° C.: | 250 |
| Range: | 0 |
| Attenuation: | 0 |
| Run time: | 25 min. |
| Oven Program: | 50° C. ramp to 260° C. at 10° C./min., hold 4 min. |

U.S. Pat. No. 8,314,119 shows synthesis of (4s)-1-azaadamantan-4-ol HCl salt from a 7-step process of: (1) Reducing of 1,4-dioxaspiro[4.5]decan-8-one with TOSMIC giving 1,4-dioxaspiro[4.5]decane-8-carbonitrile; (2) Reducing resulting product with LAH giving 1,4-dioxaspiro[4.5]decan-8-yl-methanamine; (3) Cyclizing resulting product with a double-Mannich type condensation using paraformaldehyde and sulfuric acid to form azaadamantan-4-one; (4) Reducing ketone group of azaadamantan-4-one to an alcohol using NaBH$_4$ in presence of borane-THF complex to form a diastereomeric mixture of 1-azaadamantan-4-ol N-borane complex; (5) Coupling resulting product with 4-chlorobenzoic acid; (6) Separating (4s) isomer by column chromatography (silica gel, using 3:1 hexanes-EtOAc), followed by removing 4-chlorobenzoic acid moiety with NaOH; and (7) Removing BH$_3$ group with HCl giving (4s)-1-azaadamantan-4-ol HCl salt. U.S. Pat. No. 8,314,119 is incorporated herein by reference.

The first step of the process described in U.S. Pat. No. 8,314,119 requires use of toxic TOSMIC, potentially fatal if inhaled (see Sigma-Aldrich MSDS), and thus not particularly suitable for large scale manufacture of (4s)-1-azaadamantan-4-ol due to health and safety concerns. The second step in US' 119 requires use of LAH, not particularly suitable for industrial processes (often requiring strict safety prescriptions), because LAH reacts violently with water to produce flammable gases, which may in turn result in fire or explosion (see Sigma-Aldrich MSDS). The fifth and sixth steps in US' 119 separate (r) and (s) isomers from the diastereomeric mixture using column chromatography. Column chromatography can result in lower yield and typically requires high amount of solvent, making scaling up difficult. The 7-step process described in US' 119 results in a time consuming and expensive synthetic route to (4s)-1-azaadamantan-4-ol, making industrial applicability less likely. Furthermore, the synthetic route in US' 119 utilizes toxic and highly reactive reagents, creating risk for labors preparing (4s)-1-azaadamantan-4-ol and creating environmental concerns.

Conversely, the 4-step process described in Scheme 1 involves fewer steps, reactions are more selective (i.e., isomer separation no longer required), and the process described in Scheme 1 offers workplace and environmental advantages by reducing quantities of toxic byproducts and solvents. The use of boron containing reagents is also no longer required. Furthermore, HBr salt of (4s)-1-azaadamantan-4-ol may offer greater downstream synthetic benefits, as opposed to HCl salt.

Speckamp et al., *Tetrahedron*, Vol. 50, No. 29, pg. 8853-8862 (1994) shows a 9-step synthesis of (4s)-azaadamantanol from bicyclic amine 3-azabicyclo[3.3.1]non-6-ene intermediate, using paraformaldehyde and formic acid. Two different synthetic routes are described in Speckamp for synthesis of the bicyclic amine intermediate. The first route utilizes Cu(bpy)Cl catalyst, giving 60% yield of carbamate-protected bicyclic amine intermediate as the primary product. The second route does not use a copper catalyst, giving a lower 11% yield of carbamate-protected bicyclic amine intermediate as a secondary product. In contrasting differences between the copper-catalyzed route and the copper-free route, Speckamp states " . . . in order to obtain a good yield of 11 . . . [i.e., carbamate-protected bicyclic amine intermediate]. . . . , the preferred method of catalysis is the use of Cu(bpy)Cl." Subsequent deprotection (i.e., removing carbamate protecting group), of the bicyclic amine intermediate requires extreme reaction conditions (i.e., 180° C.). The final step in Speckamp utilizes paraformaldehyde and formic acid to cyclize the bicyclic amine intermediate into tricyclic (4s)-azaadamantanol. The 9-step copper-catalyzed process in Speckamp gives (4s)-azaadamantanol in an overall yield of 22%.

Conversely, the 4-step process described in Scheme 1 achieves a yield that is three times greater than that of Speckamp, and without the use of a metal catalyst. Furthermore, the 4-step metal-free process described herein utilizes fewer reaction steps, fewer isolations and milder reaction conditions, giving (4s)-azaadamantanol in an overall yield of 75%.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A process for preparing a compound, or a salt of a compound, or a solvate thereof, of Formula (III)

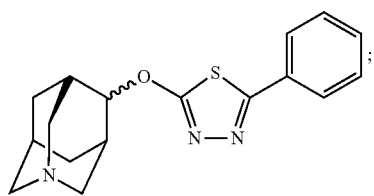
(III)

the process comprising step of contacting a compound, or a salt of a compound, or a solvate of a compound. of Formula (II)

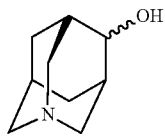
(II)

with 2-bromo-5-phenyl-1,3,4-thiadiazole, in presence of a metal (alkylsilyl)amide and a reaction medium, to form a reaction mixture, and optionally contacting the reaction mixture with citric acid.

2. Process of claim 1, wherein:

the salt of a compound of Formula (II) is

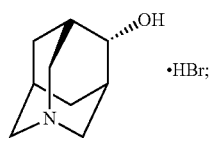
·HBr;

the reaction mixture comprises

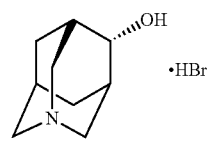
·HBr and sodium bis(trimethylsilyl)amide, wherein the reaction mixture is contacted with citric acid to form a compound of Formula (IV)

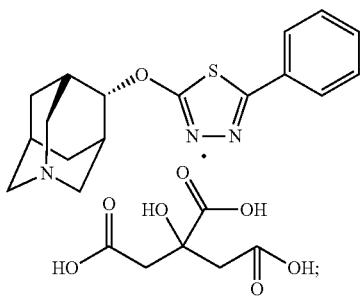
(IV)

the reaction medium comprises a polar protic solvent selected from tetrahydrofuran and ethanol.

3. A process for preparing a compound, or a salt of a compound, or a solvate thereof, of Formula (III)

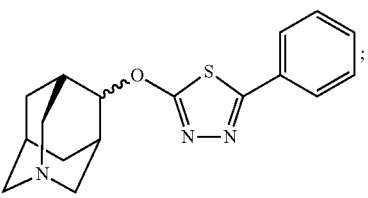
(III)

the process comprising steps of:

(a) condensing benzylamine with cyclohex-3-enecarbaldehyde to form (E)-N-(cyclohex-3-en-1-ylmethylene)-1-phenylmethanamine;

(b) contacting (E)-N-(cyclohex-3-en-1-ylmethylene)-1-phenylmethanamine with an isomerizing agent to form (E)-N-benzylidene-1-(cyclohex-3-en-1-yl)methanamine;

(c) contacting (E)-N-benzylidene-1-(cyclohex-3-en-1-yl) methanamine with an aldehyde, or with an acetal, or with a hemiacetal, in presence of formic acid and a reaction medium to form a compound of Formula (I)

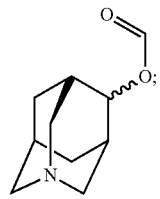
(I)

(d) contacting a compound of Formula (I) with a hydrolyzing agent in a reaction medium to form a compound, or a salt of a compound, of Formula (II)

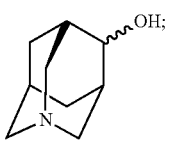
(II)

(e) contacting aminothiourea and benzoic acid in presence of polyphosphoric acid to form a 2-amino-5-phenyl-1,3,4-thiadiazole salt;

(f) contacting a 2-amino-5-phenyl-1,3,4-thiadiazole salt, a Cu(II)halide and an alkyl-nitrite, in presence of a polar aprotic solvent to form 2-bromo-5-phenyl-1,3,4-thiadiazole; and (g) contacting a compound of Formula (II) with 2-bromo-5-phenyl-1,3,4-thiadiazole, in presence of a metal (alkylsilyl)amide and a reaction medium, to form a reaction mixture, and optionally contacting the reaction mixture with citric acid.

4. Process of claim 3, wherein:

the reaction mixture comprises

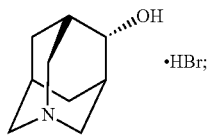

and metal (alkylsilyl)amide to form a reaction mixture, which is contacted with citric acid to form a compound of Formula (IV)

(IV)

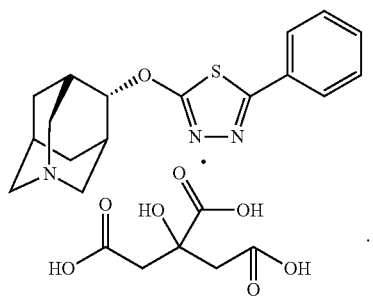

5. Process of claim 4, wherein:

the isomerizing agent is potassium tert-butoxide, wherein the potassium tert-butoxide is present in an amount ranging from about 0.05 molar equivalents to about 3.0 molar equivalents of potassium tert-butoxide to (E)-N-(cyclohex-3-en-1-ylmethylene)-1-phenylmethanamine;

the compound of Formula (I) is

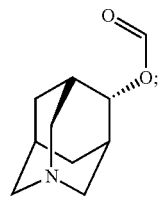

the hemiacetal is paraformaldehyde, wherein the paraformaldehyde is present in an amount ranging from about 2.0 molar equivalents to about 5.0 molar equivalents of paraformaldehyde to (E)-N-benzylidene-1-(cyclohex-3-en-1-yl)methanamine;

the hydrolyzing agent in a reaction medium is a hydrogen bromide solution comprising about 43% to about 53% w/w of hydrogen bromide, wherein the hydrogen bromide solution is present in an amount ranging from about 1.0 molar equivalent to about 2.0 molar equivalents of the hydrogen bromide solution to the compound of Formula (I);

the salt of a compound of Formula (II) is

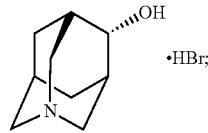

the 2-amino-5-phenyl-1,3,4-thiadiazole salt is

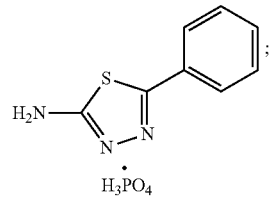

the Cu(II)halide is $CuBr_2$;
the alkyl-nitrite is iso-amyl nitrite;
the polar aprotic solvent is acetonitrile;
the metal (alkylsilyl)amide is sodium bis(trimethylsilyl)amide; and
the reaction medium comprises a polar aprotic solvent selected from tetrahydrofuran and ethanol.

* * * * *